(12) United States Patent
Prutchi et al.

(10) Patent No.: US 6,788,972 B2
(45) Date of Patent: Sep. 7, 2004

(54) IMPLANTABLE CARDIAC STIMULATOR WITH ELECTRODE-TISSUE INTERFACE CHARACTERIZATION

(75) Inventors: David Prutchi, Lake Jackson, TX (US); Patrick J. Paul, Lake Jackson, TX (US); Gregory R. Martin, Pearland, TX (US)

(73) Assignee: Intermedics Inc., Angleton, TX (US)

( * ) Notice: Subject to any disclaimer, the term of this patent is extended or adjusted under 35 U.S.C. 154(b) by 0 days.

(21) Appl. No.: 10/371,609

(22) Filed: Feb. 21, 2003

(65) Prior Publication Data

US 2003/0125779 A1 Jul. 3, 2003

Related U.S. Application Data

(62) Division of application No. 09/454,742, filed on Dec. 6, 1999, now Pat. No. 6,564,099, which is a division of application No. 09/075,144, filed on May 8, 1998, now Pat. No. 6,141,585.

(51) Int. Cl.$^7$ ................................................. A61N 1/37
(52) U.S. Cl. ............................................ 607/28; 607/8
(58) Field of Search ........................ 607/8, 28; 600/547

(56) References Cited

U.S. PATENT DOCUMENTS

| | | | |
|---|---|---|---|
| 4,245,643 A | 1/1981 | Benzing, III et al. | 128/419 PT |
| 4,337,776 A | 7/1982 | Daly et al. | 128/419 |
| 4,448,196 A | 5/1984 | Money et al. | 128/419 PT |
| 4,532,931 A | 8/1985 | Mills | 128/419 PG |
| 4,613,850 A | 9/1986 | Timmermann | 340/686 |
| 4,830,006 A | 5/1989 | Haluska et al. | 607/4 |
| 4,899,750 A | 2/1990 | Ekwall | 128/419 PG |
| 4,949,720 A | 8/1990 | Thompson | 128/419 |

(List continued on next page.)

OTHER PUBLICATIONS

Platia, E.V. ,et al. ,"Time Course of Transvenous Pacemaker Stimulation Impedance, Capture Threshold, and Electrogram Amplitude", Washington, D.C.,(Sep./Oct. 1986),pp. 620–625.

Ragheb, T., et al. ,"Electrical Properties of Metallic Electrodes", *Medical & Biological Engineering & Computing*, West Lafayette, IN,(Mar. 1990),pp. 182–186.

Schaldach, M., Bioelectric Phenomena in Cardiac Pacing, Erlangen, West Germany,(1987) pp. 0139–0142.

*Primary Examiner*—George R. Evanisko
(74) *Attorney, Agent, or Firm*—Schwegman, Lundberg, Woessner & Kluth, P.A.

(57) ABSTRACT

A cardiac stimulator capable of measuring pacing impedance includes a tank capacitor for delivering charge to the heart via device leads, a shunt resistor, and high-impedance buffers for measuring pacing current through the shunt resistor. Soon after the leading edge of the stimulation pulse, the voltage across the shunt resistor, as sampled by a high-impedance buffer, indicates lead and cardiac tissue resistance. Just prior to opening the pacing switch to terminate the stimulation pulse, the voltage across the shunt resistor is sampled by a high-impedance buffer and held once again to allow the capacitance of the lead/heart tissue to be calculated. In alternative embodiments, a high-impedance buffer measures the voltage between the tank capacitor and ground immediately following the stimulation pulse to allow estimation of the lead/heart tissue capacitance. In one alternative embodiment, a look-up table is created in main memory and searched to find the closest lead/heart tissue capacitance estimate to any arbitrary degree of accuracy. In another alternative embodiment, the lead/heart tissue capacitance is estimated by successive approximation to any arbitrary degree of accuracy. When the lead/heart tissue capacitance and lead resistance have been determined, a plurality of parameters of importance for analyzing and optimizing a cardiac stimulation system may be calculated, such as the instantaneous current, the average current, the charge, and the energy delivered to the cardiac tissue.

15 Claims, 8 Drawing Sheets

U.S. PATENT DOCUMENTS

| | | | |
|---|---|---|---|
| 4,964,407 A | 10/1990 | Baker, Jr. et al. | 128/419 PG |
| 5,003,975 A | 4/1991 | Hafelfinger et al. | 128/419 PG |
| 5,137,021 A | 8/1992 | Wayne et al. | 128/419 PT |
| 5,201,865 A | 4/1993 | Kuehn | 128/419 PT |
| 5,215,081 A | 6/1993 | Ostroff | 128/419 |
| 5,224,475 A | 7/1993 | Berg et al. | 128/419 D |
| 5,391,186 A | 2/1995 | Kroll et al. | 607/5 |
| 5,423,871 A | 6/1995 | Hoegnelid et al. | 607/28 |
| 5,431,692 A | 7/1995 | Hansen et al. | 607/28 |
| 5,534,018 A | 7/1996 | Wahlstrand et al. | 607/27 |
| 5,716,381 A | 2/1998 | Reggiardo | 607/8 |
| 5,722,997 A | 3/1998 | Nedungadi et al. | 607/28 |
| 5,755,742 A | 5/1998 | Schuelke et al. | 607/27 |
| 5,897,577 A | 4/1999 | Cinbis et al. | 607/28 |
| 6,058,325 A * | 5/2000 | Baura | 600/547 |

\* cited by examiner

IMPLANTABLE CARDIAC STIMULATOR WITH ELECTRODE-TISSUE INTERFACE CHARACTERIZATION

CROSS-REFERENCE TO RELATED APPLICATION(S)

This application is a division of U.S. patent application Ser. No. 09/454,742, filed on Dec. 6, 1999, now U.S. Pat. No. 6,564,099 which is a division of U.S. patent application Ser. No. 09/075,144, filed on May 8, 1998, now issued as U.S. Pat. No. 6,141,585, the specifications of which are incorporated by reference herein.

FIELD OF THE INVENTION

The present invention relates generally to implantable cardiac pacing systems and particularly to an improved technique for electrode-tissue interface characterization. More particularly, the present invention relates to an apparatus and method for measuring the resistive and capacitive components of the impedance of pacemaker or defibrillator leads.

BACKGROUND OF THE INVENTION

In the normal human heart, illustrated in FIG. 1, the sinus (or sinoatrial (SA)) node generally located near the junction of the superior vena cava and the right atrium constitutes the primary natural pacemaker by which rhythmic electrical excitation is developed. The cardiac impulse arising from the sinus node is transmitted to the two atrial chambers (or atria) at the right and left sides of the heart. In response to excitation from the SA node, the atria contract, pumping blood from those chambers into the respective ventricular chambers (or ventricles). The impulse is transmitted to the ventricles through the atrioventricular (AV) node, and via a conduction system comprising the bundle of His, or common bundle, the right and left bundle branches, and the Purkinje fibers. The transmitted impulse causes the ventricles to contract, the right ventricle pumping unoxygenated blood through the pulmonary artery to the lungs, and the left ventricle pumping oxygenated (arterial) blood through the aorta and the lesser arteries to the body. The right atrium receives the unoxygenated (venous) blood. The blood oxygenated by the lungs is carried via the pulmonary veins to the left atrium.

This action is repeated in a rhythmic cardiac cycle in which the atrial and ventricular chambers alternately contract and pump, then relax and fill. Four one-way valves, between the atrial and ventricular chambers in the right and left sides of the heart (the tricuspid valve and the mitral valve, respectively), and at the exits of the right and left ventricles (the pulmonic and aortic valves, respectively, not shown) prevent backflow of the blood as it moves through the heart and the circulatory system.

The sinus node is spontaneously rhythmic, and the cardiac rhythm it generates is termed normal sinus rhythm ("NSR") or simply sinus rhythm. This capacity to produce spontaneous cardiac impulses is called rhythmicity, or automaticity. Some other cardiac tissues possess rhythmicity and hence constitute secondary natural pacemakers, but the sinus node is the primary natural pacemaker because it spontaneously generates electrical pulses at a faster rate. The secondary pacemakers tend to be inhibited by the more rapid rate at which impulses are generated by the sinus node.

Disruption of the natural pacemaking and propagation system as a result of aging or disease is commonly treated by artificial cardiac pacing, by which rhythmic electrical discharges are applied to the heart at a desired rate from an artificial pacemaker. An artificial pacemaker (or "pacer") is a medical device which delivers electrical pulses to an electrode that is implanted adjacent to or in the patient's heart in order to stimulate the heart so that it will contract and beat at a desired rate. If the body's natural pacemaker performs correctly, blood is oxygenated in the lungs and efficiently pumped by the heart to the body's oxygen-demanding tissues. However, when the body's natural pacemaker malfunctions, an implantable pacemaker often is required to properly stimulate the heart. An in-depth explanation of certain cardiac physiology and pacemaker theory of operation is provided in U.S. Pat. No. 4,830,006.

Pacers today are typically designed to operate using one of three different response methodologies, namely, asynchronous (fixed rate), inhibited (stimulus generated in the absence of a specified cardiac activity), or triggered (stimulus delivered in response to a specified hemodynamic parameter). Broadly speaking, the inhibited and triggered pacemakers may be grouped as "demand" type pacemakers, in which a pacing pulse is only generated when demanded by the heart. To determine what pacing rate is required by the pacemaker, demand pacemakers may sense various conditions such as heart rate, physical exertion, temperature, and the like. Moreover, pacemaker implementations range from the simple fixed rate, single chamber device that provides pacing with no sensing function, to highly complex models that provide fully automatic dual chamber pacing and sensing functions. The latter type of pacemaker is the latest in a progression toward physiologic pacing, that is, the mode of artificial pacing that most closely simulates natural pacing.

Referring now to FIG. 2, a conventional implantable medical device 200 is shown implanted and coupled to a patient's heart 250 by leads 205 and 210. The implantable medical device 200 may include a pacemaker or defibrillator or any medical device that performs pacing or defibrillating functions. The implanted medical device 200 (or simply "pacer") also includes a housing or "can" 215 which houses a battery and pacing or defibrillating circuitry (not shown). In the dual chamber pacing arrangement shown, leads 205 and 210 are positioned in the right ventricle and right atrium, respectively. Each lead 205 and 210 includes at least one stimulating electrode for delivery of electrical impulses to excitable myocardial tissue in the appropriate chamber(s) in the right side of the patient's heart. As shown in FIG. 2, each lead 205 and 210 includes two electrodes. More specifically, lead 210 includes ring electrode 230 and tip electrode 235, and lead 205 includes ring electrode 220 and tip electrode 225. Two, three, and four terminal devices all have been suggested as possible electrode configurations.

A lead configuration with two electrodes is known as a "bipolar lead." Such a configuration typically consists of a pair of wires arranged coaxially and individually insulated. Each of the wires may consist of multiple wire strands wrapped together for redundancy. A circuit consisting of the pacemaker 200 and the heart muscle can be formed by connecting the lead electrodes to different portions of the heart muscle. In a bipolar configuration, electric current impulses generally flow from the ring electrode through the heart muscle to the tip electrode, although current may travel from the tip electrode to the ring electrode in alternative configurations. A lead with one electrode is known as a "unipolar lead." In a unipolar configuration, the pacemaker can 215 functions as an electrode. Current flows from the unipolar lead through the heart tissue, returning to the pacer via the can 215.

In general, a pacing pulse current is formed by the flow of charge carriers in the circuit formed by the lead and tissue. Because the electrode is typically composed of a solid conductive material, while the myocardial tissue consists of liquid electrolyte, the electrode forms an electrode/electrolyte interface through which the charge carriers pass. Accordingly, electron conductivity accounts for charge transfer in the lead circuit and in the solid phase of the electrode interface, while ion conductivity is the primary mechanism responsible for charge flow through the electrolyte interface and tissues.

At the interface layer, pacing pulse charge flows from the solid phase of the electrode interface to the electrolyte phase until the electrochemical potential of the electrode interface balances the electrochemical potential of the electrolyte interface. During such a process, an electric charge layer, known as the Helmholtz layer, forms around the surface of the electrode. While the exact nature of the Helmholtz layer is very complex, it can be generally modeled as an electric circuit using voltage sources, diodes, and/or devices that contribute impedance (which is the ability to impede electric current) to the lead-tissue circuit. Electrical impedance may be generally characterized by the combination of a resistive component, such as a resistor, with a reactive component, such as a capacitor or inductor. One Helmholtz layer model includes a polarization potential (known as the "Helmholtz voltage") in series with the parallel combination of a resistor (known as the "Warburg resistor") and a capacitor (known as the "Helmholtz capacitor"). A second Helmholtz layer model has been suggested which consists of an impedance circuit shunted by two zener diodes. The second configuration accounts for the electrical behavior of heart tissue when the interface voltage exceeds several hundred millivolts. A simple yet accurate model of the Helmholtz layer consists of the Warburg resistance in series with a voltage-dependent Helmholtz capacitance, eliminating the need to model the polarization potential.

FIG. 3A illustrates a model of a conventional cardiac stimulator circuit consisting of a pacer 200, heart tissue 250, and bipolar pacer lead 205 terminated by tip electrode 225 and ring electrode 220. Ring electrode 220 and tip electrode 225 couple the pacer 200 to different portions of the heart tissue 250. Alternatively, a model as in FIG. 3B using a unipolar lead 305 would include a single electrode 320 coupled to the heart tissue 250 with the pacer can 215 coupled to the chest tissue, labeled as ground. In the unipolar configuration of FIG. 3B, the pacer 200 sends electric current from the pacer can 215 to a single electrode 320 through the chest and heart tissue 250. Accordingly, the impedance introduced by the combination of chest tissue (FIG. 3B only), bipolar lead 205 or unipolar lead 305, and heart tissue 250 may be collectively modeled by resistor R3 (the Warburg resistor) in series with capacitor C3 (the Helmholtz capacitor).

Such models as shown in FIGS. 3A and 3B are important for delivering "pacing impedance" estimates, which help to indicate the condition of the pacer leads as well as to estimate electric charge, current, and energy delivered to the heart tissue. Particularly, deviations that occur over time in the pacing impedance serve to indicate the conditions related to the pacing or defibrillation lead system. Such conditions include electrode micro-dislocation, lead impedance changes, evaluation of electrode suitability for detecting evoked potentials, and methods for detecting changes in the excitable tissue as a function of catecholamine concentration, metabolic changes, and ischemia. In addition, the charge, current, energy, and impedance measurements allow physicians to estimate the longevity of the implanted device. Accordingly, pacing impedance estimates aid physicians in maintaining and optimizing pacemaker operation throughout the life of the device.

Although a purely resistive lead impedance estimate may provide a means for a rough estimate of pacer and battery condition, such an estimate may deviate significantly from the true impedance in some situations, since the physical and electrochemical properties that lead to the Helmholtz layer change with variations in the electric field intensity which develops at the electrode-electrolyte interface. For example, corrosion, electrocatalysis of glucose and amino acids, and hydrogen ion potentiodynamics drastically alter the modeled capacitance, resistance, and polarization of the interface, as do electrode current density and electric field strength. Further, the Helmholtz capacitance varies according to a parameter known as the "microsurface area" of the electrode. The microsurface area of the electrode is the total surface area of the electrode material, including microscopic details such as porosity and other microscopic details. Typically, the Helmholtz capacitance equals about 100 microfarads ($\mu$F) per square centimeter of microsurface area. In addition, the resistance, capacitance, and polarization voltage of the Helmholtz layer can vary according to the duration and amplitude of the pacing pulse, although these properties are approximately constant for pulse widths of less than 0.5 milliseconds (ms) and pulse amplitudes of less than 0.5 volts (V).

Methods for measuring the resistive component of pacing impedance have been available for some time as part of the information that implantable pacemakers and defibrillators can collect and telemeter. However, such estimates have neglected the reactive impedance component, as modeled by the Helmholtz capacitance, resulting in an incomplete characterization of the pacing impedance. Such omissions produce undesirable impedance estimation errors which may propagate into subsequent calculations of charge, current, and energy delivered to the heart tissue as well as other conditions closely related to the pacing impedance. Impedance-based methods for monitoring the leads and electrodes of implantable cardiac stimulators have been described in a number of patents, including U.S. Pat. No. 4,899,750, U.S. Pat. No. 5,201,865, and U.S. Pat. No. 5,534,018 which disclose devices for estimating the resistive lead impedance component.

While measurement of the Helmholtz capacitance has been suggested using alternating current (AC) circuits, such circuits are not practical for use with cardiac stimulation devices, which typically use direct current (DC) pulses for cardiac stimulation. Accordingly, devices using AC methods must operate exclusively of normal pacemaker/defibrillator operation. Therefore, no practical device or method for estimating both the resistive and reactive components of pacer lead impedance has been devised within a cardiac stimulator, and present-day cardiac stimulators must tolerate the inaccuracies introduced by purely resistive impedance estimates, as described above.

For the foregoing reasons, a practical apparatus for measuring both the resistive and capacitive components of the lead impedance, including the Helmholtz layer, would greatly improve the implementation of implanted stimulation devices. Such an apparatus, if devised, should be adapted to measure lead impedance during normal operation of the implanted device without affecting the functionality of the pacing or defibrillating circuit. The resulting device would significantly improve the accuracy of cardiac impedance estimates, resulting in superior optimization and maintenance of implanted devices. Unfortunately, to date, no such device is known that provides these features.

SUMMARY OF THE INVENTION

Accordingly, there is provided herein a cardiac stimulator including a pulse generator for delivering current to the heart tissue, an impedance measurement circuit coupled to the pulse generator, and a processor for performing control and calculation functions. Upon receiving control signals from the processor, the pulse generator transmits electric current (known as a pacing pulse) from a charged capacitor into the heart tissue. At the same time, the processor asserts control pulses to the impedance circuit, causing the impedance circuit to sample voltages from the pulse generator. The impedance circuit records the voltage measurements through sample-and-hold units, transmitting the voltages as signals to the processor. Using these voltage measurements, the processor calculates the impedance of the lead/tissue circuit.

The pulse generator includes a tank capacitor for delivering charge to the heart via device leads and a pacing voltage source for charging the tank capacitor through an electronically-controlled charge switch. Just prior to the time that the pacing pulse is to be delivered to the heart tissue, the charge switch is opened. A pacing switch is then closed to allow charge from the tank capacitor to flow through a DC-blocking capacitor into the lead and subsequently the heart. Opposing the flow of this current are the resistance of the pacing switch, the resistive components of the lead and load impedance (i.e., the lead resistance and ionic resistance), the Helmholtz capacitance, and a current-measurement-shunt resistor.

Soon after the leading edge of the pacing pulse, or at time $t=(0^+)$, the voltage across the current-measurement-shunt resistor is sampled through a high-impedance buffer and held. Since the DC-blocking and Helmholtz capacitances have not charged appreciably at $t=(0^+)$, they behave as short-circuits. The pacing circuit is therefore purely resistive, and the lead and ionic resistance may be calculated by the method of circuit analysis.

Just prior to opening the pacing switch to terminate the pacing pulse, or at time $t=(T_{PW}-)$, the voltage across the current-measurement-shunt resistor is sampled by a high-impedance buffer and held once again to allow the Helmholtz capacitance to be calculated. After the pacing pulse is delivered and before the tank capacitor is recharged, the end voltage of the tank capacitor is sampled through a high-impedance buffer and held. Concurrently with the sampling of the tank capacitor end voltage, the DC-blocking capacitor discharges into the human body by an active discharge switch and a passive-discharge resistor. In a preferred embodiment, the resistive and capacitive components of the lead impedance may be calculated explicitly using the shunt resistor voltage samples from the high-impedance buffers.

In other embodiments, the apparatus estimates the Helmholtz capacitance without knowledge of the voltage across the current-measurement-shunt resistor just prior to the end of the pulse. The voltage across the tank capacitor after the pulse ends, i.e. at $t=(T_{PW}+)$, may be expressed using a formula based on pacing voltage, tank capacitance, DC-blocking capacitance, Helmholtz capacitance, current-measurement-shunt resistance, pacing switch resistance, lead/tissue resistance, and pulse width, all of which are known values except the Helmholtz capacitance and lead/tissue resistance. The tank voltage formula consists of an exponential term multiplied by a constant term and added to an additive term. All three terms include the Helmholtz capacitance as a variable. If the tank capacitor voltage is measured following the pulse and the lead/tissue resistance is calculated using circuit analysis as above, then the formula reduces to an equation involving only one unknown variable, the Helmholtz capacitance.

In an alternative embodiment, a look-up table is created in main memory by using the calculated Warburg resistance combined with known values of the pacing voltage, tank capacitance, DC-blocking capacitance, current-measurement-shunt resistance, pacing switch resistance, and pulse width in the formula along with a series of empirical estimates for the value of the Helmholtz capacitance. The formula produces a distinct tank capacitor voltage calculation for each Helmholtz capacitance estimate. The Helmholtz capacitance estimates along with the calculated tank capacitor voltages are stored into main memory as a look-up table, and the actual, measured tank capacitor voltage is compared with the set of calculated tank capacitor voltages. Searching through the look-up table, the apparatus chooses the Helmholtz capacitance estimate as the empirical estimate which produced a calculated tank capacitor voltage that most closely resembles the measured tank capacitor voltage.

In another embodiment, a single empirical estimate for the Helmholtz capacitance is substituted into the one part of the formula, either into the exponential term or into the additive and constant terms. The remaining term(s) may be reduced algebraically to solve for the unknown Helmholtz capacitance value. If the resulting calculation of the Helmholtz capacitance value does not agree with the originally substituted empirical estimate, then an updated empirical estimate is substituted into the first term(s), and a new Helmholtz capacitance is calculated using the remaining term(s). If the resulting calculation of the Helmholtz capacitance value lies within an acceptable range of the originally substituted empirical estimate, then the measured Helmholtz capacity is determined as the final empirical estimate. Such an approximation is simple to compute using conventional circuitry and can conform to any arbitrary level of accuracy by iterating through the equation with progressively better estimates for the Helmholtz capacitance.

When the Helmholtz capacitance and Warburg resistance have been determined, a plurality of parameters of importance for analyzing and optimizing a pacing system may be calculated, including the current delivered to the cardiac tissue at any instantaneous point in time, the average current delivered to the cardiac tissue over the duration of the pulse, the total charge and the total energy delivered to the cardiac tissue and to the leads, and the Helmholtz potential after pacing polarization.

Thus, the present invention comprises a combination of features and advantages that enable it to substantially advance the art by providing an apparatus for gauging both the resistive and capacitive components of the Helmholtz layer. These and various other characteristics and advantages of the present invention will be readily apparent to those skilled in the art upon reading the following detailed description of the preferred embodiments of the invention and by referring to the accompanying drawings.

BRIEF DESCRIPTION OF THE DRAWINGS

A better understanding of the present invention can be obtained when the following detailed description of the preferred embodiment is considered in conjunction with the following drawings, in which.

DETAILED DESCRIPTION OF PREFERRED EMBODIMENTS

Figure 4:
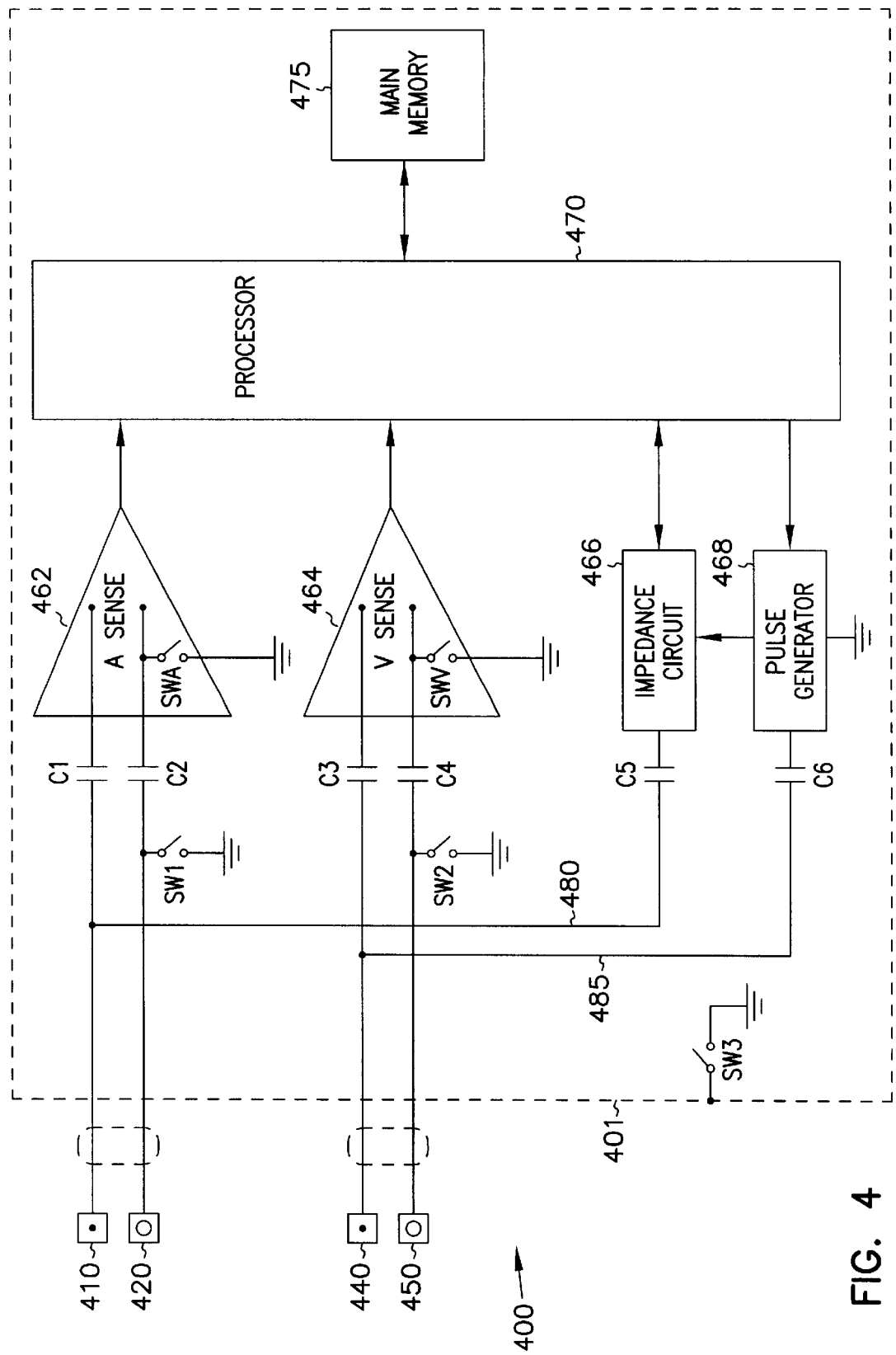
FIG. 4 is an exemplary block diagram of a cardiac stimulator made in accordance with the present invention.

An exemplary cardiac stimulator 400 made in accordance with the present invention is illustrated in the block diagram of FIG. 4. The cardiac stimulator 400 may be a pacemaker, a defibrillator, or any or implantable cardiac stimulator. The cardiac stimulator 400 generally includes atrial and ventricular sense circuits 462 and 464, a processor 470, main memory 475, an impedance circuit 466, and a pulse generator 468, all housed in enclosure, or "can" 401. The exemplary embodiment of FIG. 4 shows cardiac stimulator 400 with four leaded electrodes, namely atrial tip and ring electrodes 410 and 420, respectively, and ventricular ring and tip electrodes 440 and 450, respectively. Can 401 may function as an additional electrode in accordance with known techniques. The invention, however, may be practiced using any number of electrodes implanted in any chamber of the heart and in any configuration.

Referring still to FIG. 4, electrodes 410 and 420 couple to the atrial sense circuit 462 via capacitors C1 and C2, respectively, which are preferably 0.15 microfarad ($\mu F$) capacitors. Similarly, electrodes 440 and 450 couple to the ventricular sense circuit 464 via capacitors C3 and C4, respectively, which are also preferably 0.15 $\mu F$ capacitors. The atrial sense circuit 462 processes signals received from the atrial chamber of the heart via the atrial electrodes 410 and 420, while the ventricular sense circuit 464 processes signals received from the ventricular chamber via the ventricular electrodes 440 and 450. The atrial and ventricular sense circuits 462 and 464 generally include a low power, highly sensitive amplifier, a band pass filter, and a threshold detector (not shown). The atrial 462 and ventricular 464 circuits further include internal pulldown switches $SW_A$ and $SW_V$, respectively, the states of which are controlled by the processor 470. The amplifier amplifies the electrical signal from the associated electrodes, and the band pass filter attenuates signals whose frequencies are outside the range of frequencies known to correspond to cardiac signals. The threshold detector compares the amplified and filtered signal to a reference signal to determine when a cardiac event (also referred to as a "sense event") has occurred. If the magnitude of the amplified and filtered cardiac signal exceeds the reference signal, the processor 470 determines that a sense event has occurred. The processor 470 may then pace the heart based either on detecting or not detecting sense events via pulse generator 468 and electrodes 401, 410, 420, 440, and 450. For example, the processor 470 may initiate a ventricular pacing pulse if an atrial sense event has not been detected within a predetermined period of time following a previous atrial sense event.

Cardiac stimulator 400 further includes lead switches SW1 and SW2 as well as can switch SW3 for configuring unipolar and bipolar sensing modes and also unipolar and bipolar pacing modes, as described below. Switches SW1, SW2, and SW3 are preferably processor-controlled, single-pole single-throw (SPST) switches. When closed by the processor 470, the atrial lead switch SW1 couples the atrial ring electrode 420 to ground. Similarly, the ventricular lead switch SW2, when closed by the processor 470, couples the ventricular ring electrode 450 to ground. Can switch SW3, when closed by the processor 470, couples the can 401 to ground.

For atrial sensing using bipolar leads, atrial lead switch SW1, atrial internal pulldown switch $SW_A$, and can switch SW3 are all preferably open. In this configuration, the atrial sense circuit 462 receives a differential sense signal from tip 410 and ring 420 electrodes, respectively. For atrial sensing using a unipolar lead configuration, atrial lead switch SW1 remains open, but atrial internal pulldown switch $SW_A$ and atrial can switch SW3 are preferably closed.

Ventricular sensing operates in substantially the same manner. For ventricular sensing using bipolar leads, ventricular lead switch SW2, ventricular internal pulldown switch $SW_V$, and can switch SW3 are all preferably open. In this configuration, the ventricular sense circuit 464 receives a differential sense signal from tip 440 and ring 450 electrodes, respectively. For ventricular sensing using a unipolar lead configuration, ventricular lead switch SW2 remains open, but ventricular internal pulldown switch $SW_V$ and can switch SW3 are preferably closed.

The pulse generator 468 produces an appropriate electrical pulse to stimulate the desired chamber of the heart to beat. The processor 470 initiates the pulse generator 468 to produce a pacing pulse, and the pulse generator responds by delivering the pacing pulse to the desired chamber of the heart. The pulse generator 468 preferably includes a rate limiter to prevent the processor 470 from erroneously pacing the heart at an excessively high rate. The pulse generator 468 preferably couples to the atrial tip electrode 410 via an atrial pulse line 480 in series with a DC-blocking series capacitor C5 and further couples to ventricular tip electrode 440 via a ventricular pulse line 485 in series with a DC-blocking series capacitor C6. Further, the pulse generator 468 couples to ground to provide a circuit return path for pacing pulses. Hence, the pulse generator 468 may send a pacing pulse to the atrial or ventricular chamber via atrial pulse line 480 or ventricular pulse line 485, respectively.

In addition to selecting atrial or ventricular sensing, switches SW1, SW2, and SW3 configure the cardiac stimulator 400 for unipolar or bipolar pacing. For atrial bipolar pacing, atrial lead switch SW1 is preferably closed (therefore coupled to ground), and can switch SW3 is open. This bipolar pacing configuration allows a pacing pulse issued to the atrial chamber via atrial pulse line 480 and atrial tip electrode 410 to complete a circuit path to the pulse generator 468 through atrial ring electrode 420, which couples to ground. Ventricular bipolar pacing occurs in substantially the same manner, with ventricular lead switch SW2 closed (therefore coupled to ground) and can switch SW3 open. A pacing pulse issued to the ventricular chamber via ventricular pacing line 485 is then allowed to complete a circuit path to the pulse generator 468 through ventricular ring electrode 450, which couples to ground.

For unipolar stimulation, can switch SW3 is closed, and atrial lead switch SW1 (for stimulation of the atrial chamber) or ventricular lead switch SW2 (for stimulation of the ventricular chamber) is opened. In this unipolar pacing configuration, a pacing pulse issued to the atrial chamber via atrial pacing line 480 and atrial tip electrode 410 is allowed to complete a circuit path to the pulse generator 468 via the can 410, which is coupled to ground. Similarly, a pacing pulse issued to the ventricular chamber via ventricular pacing line 485 and ventricular tip electrode 450 is allowed to complete a circuit path to the pulse generator 468 via the can 410, which is coupled to ground.

Main memory 475 couples to the processor 470 and is capable of storing program instructions and other data to be retrieved or updated by the processor 470. Accordingly, cardiac stimulator 400 may be programmed through instructions stored in main memory to operate in one of a number of pacing modes. For example, the cardiac stimulator 400 may be programmed to sense electrical activity in the atrium, and then to pace the ventricle following a predetermined time delay after the occurrence of an atrial sense event if the ventricle has not contracted on its own. Additionally, the processor 470 may be programmed to store sense data, impedance data, or other information in main memory 475 to be retrieved at later date either by the processor 470 or by a physician.

Figure 1:
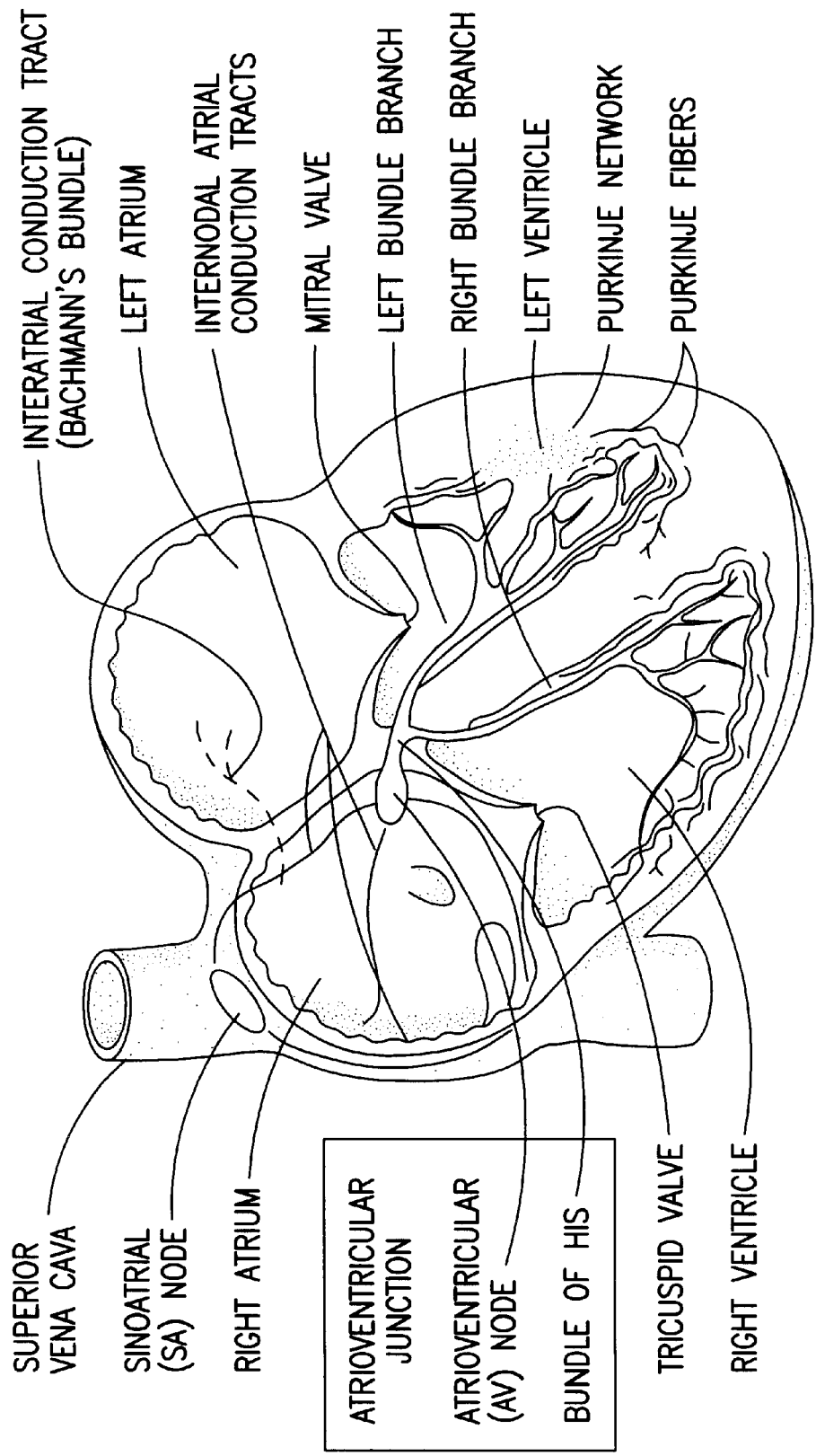
FIG. 1 illustrates the human heart.
Figure 2:
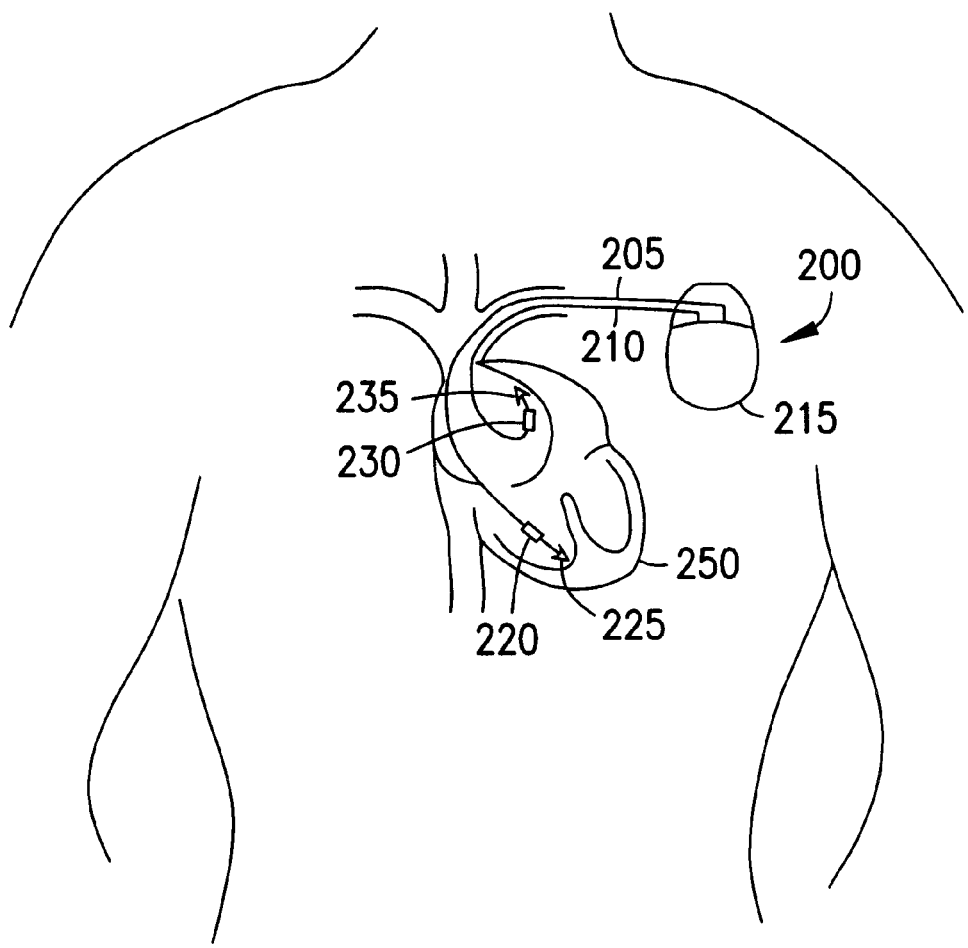
FIG. 2 shows the typical connections between a conventional pacer-defibrillator and the human heart.
Figure 3A:
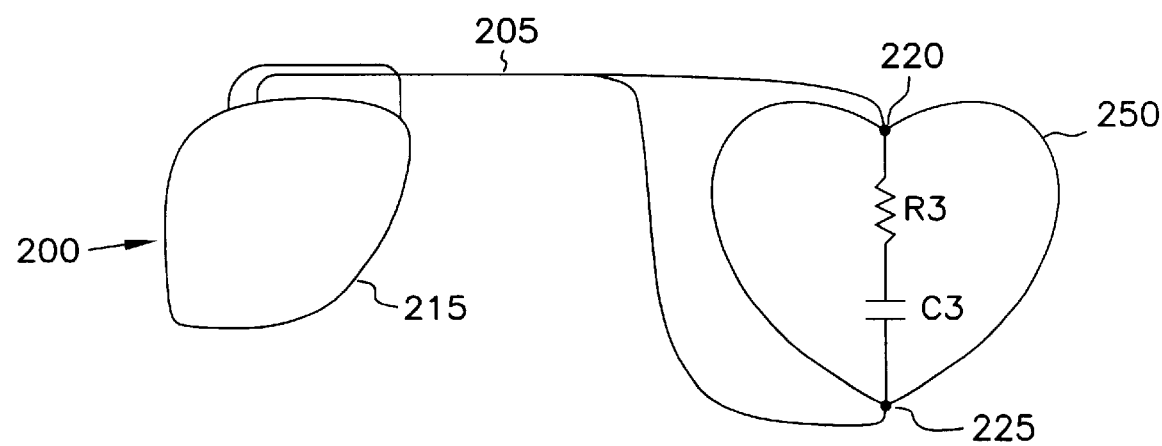
FIG. 3A is a known model of the Helmholtz circuit for a bipolar lead configuration.
Figure 3B:
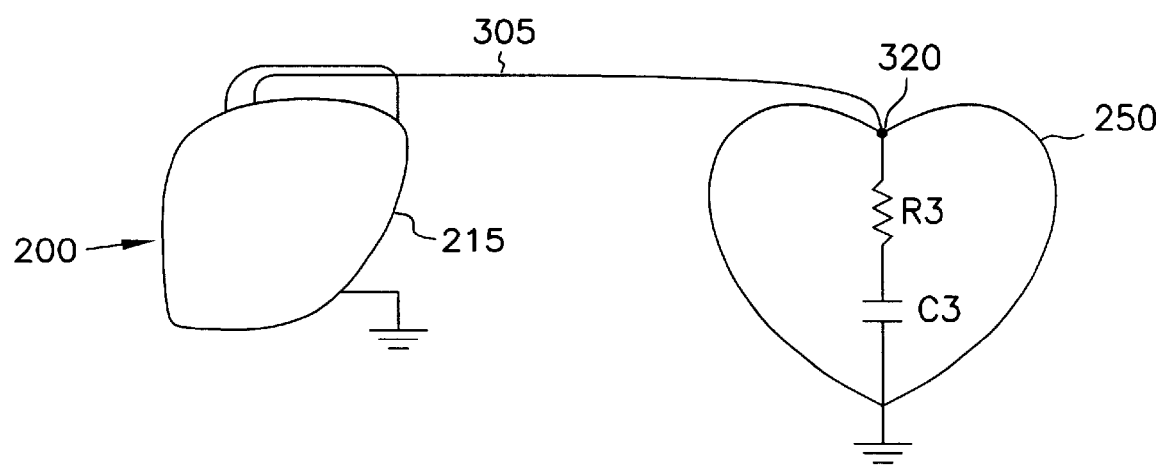
FIG. 3B is a known model of the Helmholtz circuit for a unipolar lead configuration.

Cardiac stimulator 400 uses an impedance circuit 466 to determine the electrical impedance of the lead and heart tissue circuit, as modeled by FIGS. 3A and 3B. The impedance circuit 466 generally processes the electrical signal from the pulse generator 468 and provides one or more output status signals to the processor 470. The processor 470 uses the status signal from the impedance circuit 466 to compute the impedance of the lead/heart tissue, as described in more detail below.

Figure 5:
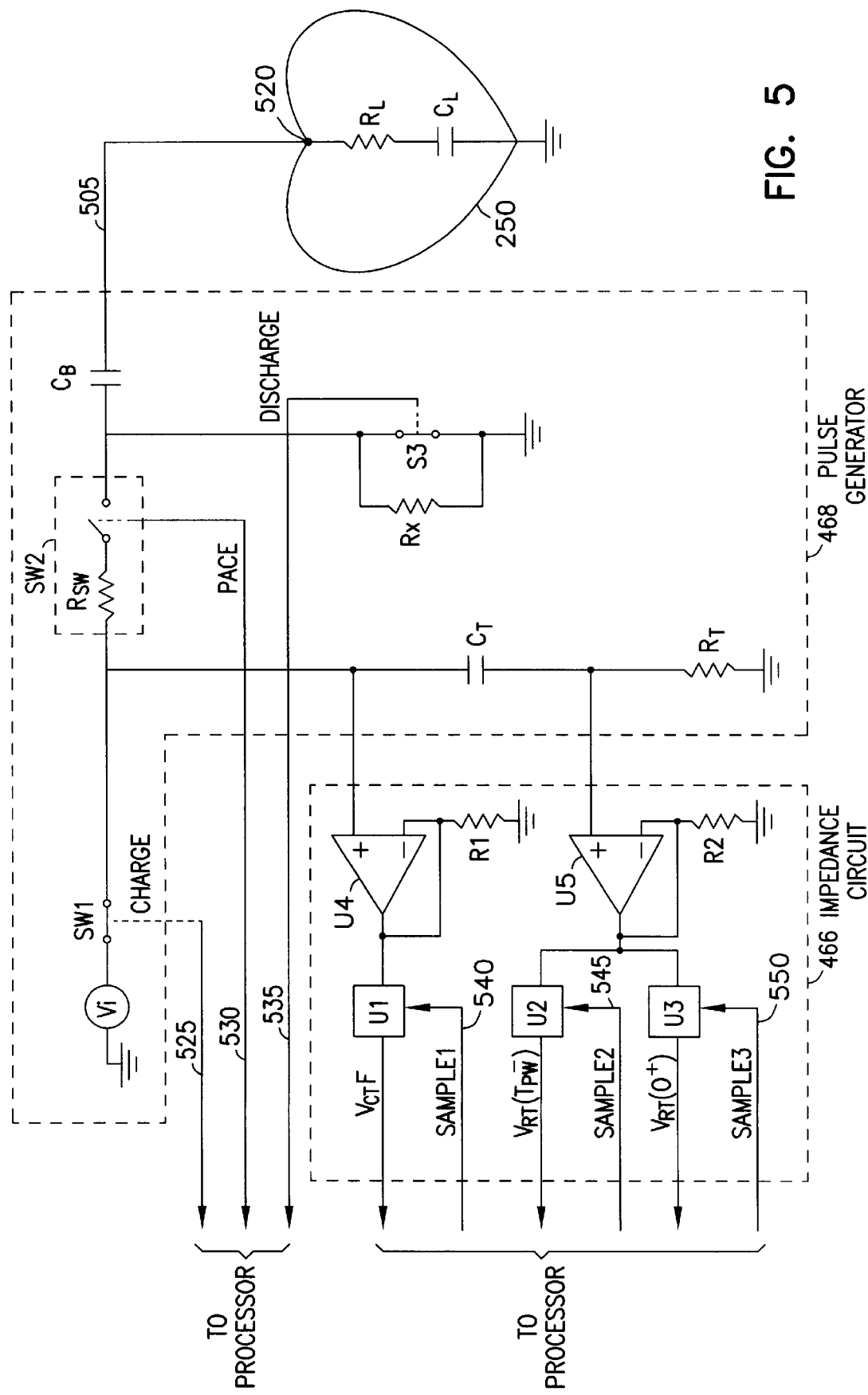
FIG. 5 is a block diagram of the impedance circuit and pulse generator circuit of the cardiac stimulator shown in FIG. 4.

FIG. 5 illustrates the electrical characteristics of the resistance of lead 505 combined with the impedance inherent in heart 250. Resistor $R_L$ generally represents the combined resistance of the lead 505 and the heart 250, while $C_L$ represents the Helmholtz capacitance described previously. Note that $R_L$ and $C_L$ do not depict actual components in the present invention but represent a model of the lead/heart tissue impedance to be determined. Cardiac stimulator 400 calculates lead/tissue resistance $R_L$ and Helmholtz capacitance $C_L$ in accordance with the methods described below. Referring still to FIG. 5, a preferred embodiment of a pulse generator 468 is shown coupled to heart 250 via lead 505. Pulse generator 468 comprises a voltage source $V_i$, a charge switch SW1, a pacing switch SW2, tank capacitor $C_T$, current-measurement-shunt resistor $R_T$, a discharge switch SW3, discharge resistor $R_X$, and DC-blocking capacitor $C_B$.

Voltage source $V_i$ is any suitable voltage source for charging tank capacitor $C_T$. Voltage source $V_i$ typically comprises a battery which may or may not be rechargeable and a programmable voltage multiplier. Voltage source $V_i$ couples to charging switch SW1, which preferably is a single-pole/single-throw (SPST) switch controlled by a processor such as processor 470 in FIG. 4, via a charge control signal 525. Tank capacitor $C_T$ and shunt resistor $R_T$ couple in series between charging switch SW1 and ground, with $C_T$ connected directly to SW1 and $R_T$ connected directly to ground. One terminal of pacing switch SW2 connects between charge switch SW1 and tank capacitor $C_T$ while the other terminal of switch SW2 connects to a DC-blocking capacitor $C_B$, discharge switch SW3, and discharge resistor $R_X$. Pacing switch SW2 is preferably an SPST switch with an internal switch resistance $R_{SW}$. Processor 470 controls the state of pacing switch SW2 via a pace control signal 530. Switch SW3 likewise is a processor-controlled, SPST switch, coupling to the processor 470 via a discharge control signal 535. Discharge switch SW3 and discharge resistor $R_X$ further couple in parallel and connect to ground. Discharge resistor $R_X$ preferably has a very high resistance compared with shunt resistor $R_T$, switch resistance $R_{SW}$, and lead/tissue resistance $R_L$. A preferred embodiment includes a shunt resistor $R_T$ of 22 Ω (ohms), a switch resistance $R_{SW}$ of 10 Ω, a discharge resistor $R_X$ of 100 Ω, and a typical lead/tissue resistance of 500 Ω.

Lead 505 couples to DC-blocking capacitor $C_B$ and terminates to electrode 520 at the heart 250. While lead 505 preferably comprises either a bipolar or unipolar lead, it is illustrated in FIG. 5 as a unipolar lead for simplicity. As one of ordinary skill in the art would recognize, the circuits of FIGS. 3A and 3B are substantially the same, since the ground node essentially serves as a lead substitute by providing a current path from the cardiac stimulator 400 to the heart. Thus, the circuit of FIG. 5 applies equally to both bipolar and unipolar lead configurations.

Impedance circuit 466 preferably comprises three sample-and-hold units U1, U2, and U3, as well as a pair of high-impedance buffers U4 and U5. Each buffer U4 and U5 may comprise any buffer circuit configured as a voltage follower with high-impedance inputs. The buffers U4 and U5 in the present embodiment are shown as unity-gain operational amplifiers (or "op-amps"), with each buffer output coupled directly to the inverting input (−) of the same buffer. Alternatively, the buffers may consist of any device that amplifies an input signal. The inverting inputs of buffers U4 and U5 connect to resistors R1 and R2, respectively, which also couple to ground. The noninverting input (+) of buffer U4 couples to tank capacitor $C_T$, charging switch SW1, and pacing switch SW2. The noninverting input of buffer U5 couples to the junction between tank capacitor $C_T$ and shunt resistor $R_T$. The output of buffer U4 drives the input of sample-and-hold unit U1. The output of buffer U5 drives both sample-and-hold units U2 and U3.

The sample-and-hold units are controlled by the processor via signals sample1 540 (U1), sample2 545 (U2), and sample3 550 (U3). When a sample control signal 540, 545, or 550 is asserted or pulsed, the corresponding sample-and-hold unit instantaneously samples the voltage appearing on its input terminal and holds that voltage on its output terminal even after the input signal is changed or removed. As described below, the output signals from sample-and-hold units U1, U2, and U3 represent voltages measured in the pulse generator 468. In a preferred embodiment, voltages are sampled at specific times in relation to the pacing pulse. For a pacing pulse with a duration of $T_{PW}$ seconds, sample-and-hold unit U3 will sample the shunt resistor voltage just after the beginning of the pacing pulse, sample-and-hold unit U2 will sample the shunt resistor voltage just before the end of the pacing pulse, and sample-and-hold unit U1 will sample the tank capacitor voltage following the pacing pulse. A more detailed explanation of these voltages readings is presented below, with respect to FIG. 6. The high-impedance nature of buffers U4 and U5 insures that the pulse generator 468 voltages are measured with negligible interference to the pulse generator 468.

Still referring to FIG. 5, voltage source $V_i$ charges tank capacitor $C_T$ to a voltage substantially equivalent to $V_i$ when the charging switch SW1 is closed. When the charging switch SW1 and discharging switch SW3 are opened and pacing switch SW2 is subsequently closed, the tank capacitor $C_T$ and shunt resistor $R_T$ are effectively switched into a resistive-capacitive (or "RC") charging circuit including switch resistance $R_{SW}$, discharge resistor $R_X$, DC-blocking capacitor $C_B$, lead/tissue resistance $R_L$, and Helmholtz capacitance $C_L$. Thus, the charge stored in $C_T$ discharges into $R_T$, $R_{SW}$, $R_X$, $C_B$, $R_L$, and $C_L$.

Figure 6:
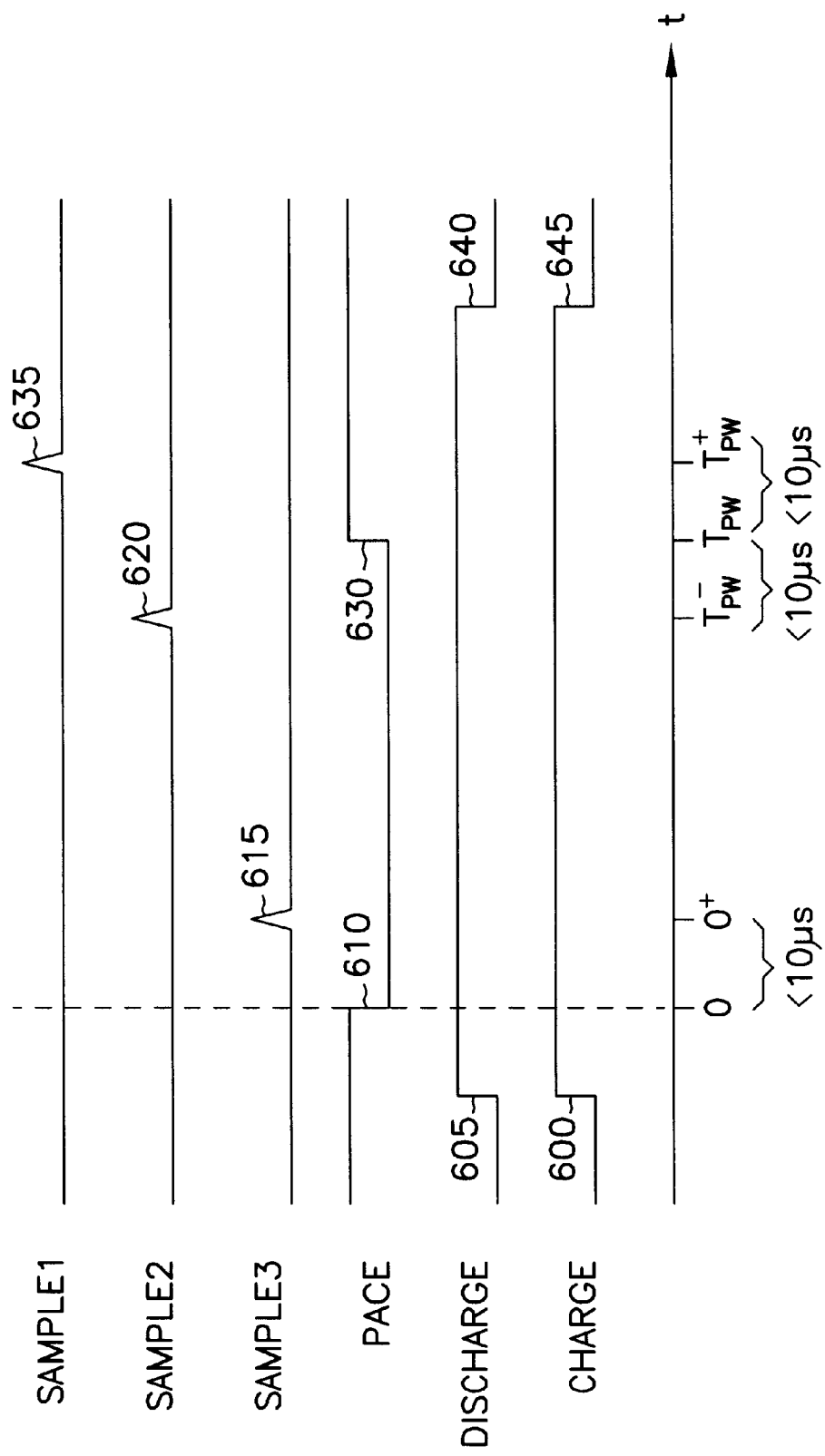
FIG. 6 is a timing diagram showing the control signals asserted by the processor of the cardiac stimulator shown in FIG. 4.

FIG. 6 illustrates a detailed timing diagram of the control signals sample1, sample2, sample3, pace, discharge, and charge which are asserted by the processor 470 of FIG. 5 to control the pulse generator 468 and impedance circuit 466. In the diagram of FIG. 6, the pacing pulse begins at t=0 and preferably extends for a duration of $T_{PW}$ seconds. Prior to the beginning of the pacing pulse, the charge and discharge signals are held low, or asserted, causing the charging switch SW1 and discharging switch SW3 to close. Also prior to the beginning of the pacing pulse, the pace signal is held high, or deasserted, causing the pacing switch SW2 to open. Thus, the tank capacitor $C_T$ charges to $V_i$ volts. In a preferred embodiment, sample1, sample2, and sample3 remain low prior to the beginning of the pacing pulse at time t=0, indicating that the previous samples are being held at the outputs of sample-and-hold units U1, U2, and U3. The tank capacitor $C_T$ becomes sufficiently charged prior to time t=0, and the processor 470 deasserts the charge and discharge signals at points 600 and 605, respectively.

The pacing pulse begins at time t=0 when the processor 470 asserts the pace signal (point 610) to a logic low state, allowing charge from the tank capacitor CT to begin flowing into the lead/tissue circuit. At time t=0, which preferably is less than 10 μs after time t=0, the processor 470 pulses sample3 (point 615), causing sample-and-hold unit U3 to record the voltage $V_{RT}(0^+)$ across the shunt resistor $R_T$. The tank capacitor CT continues to discharge until the end of the pacing pulse at time t=$T_{PW}$, which is marked by point 630. At time t=$T_{PW}$−, however, which preferably occurs approximately 10 μs or less before time t=$T_{PW}$, the processor 470 pulses sample2 (point 620), causing sample-and-hold unit U2 to record the voltage $V_{RT}(T_{PW}-)$ across the shunt resistor.

At time t=$T_{PW}$, the processor 470 halts the pacing pulse by deasserting the pace signal (point 630) to a logic high state. Subsequently, the electric charge accumulated in the DC-blocking capacitor $C_B$ and the Helmholtz layer (represented by $C_L$) begins to discharge to ground through the discharge resistor $R_X$. In alternative embodiments, the processor pulses sample1 (point 635) at time $T_{PW}$ which preferably occurs approximately 10 μs or less after time t=$T_{PW}$. Next, the processor 470 asserts the discharge and charge signals at points 640 and 645, respectively. The discharge signal allows any electric charge remaining in the DC-blocking capacitor $C_B$ and Helmholtz layer ($C_L$) to quickly discharge, while the charge signal causes voltage source $V_i$ to charge tank capacitor $C_T$ in preparation for delivering the next pacing pulse.

Any capacitor behaves as a short-circuit for a short time after current is applied to that capacitor. Thus, immediately after tank capacitor $C_T$ and shunt resistor $R_T$ are switched into the charging circuit, or at time t=$0^+$, the current in the charging circuit equals the voltage held by $C_T$ divided by the resistance presented by the resistive circuit of $R_X$, $R_T$, $R_{SW}$, and $R_L$. At the same time, processor 470 asserts control signal sample3, causing sample-and-hold unit U3 to sample and hold the voltage drop $V_{RT}(0^+)$ across shunt resistor $R_T$. Because the voltage drop across any resistor is proportional to the current flowing through that resistor, the voltage $V_{RT}(0^+)$ can be used to determine the current flowing through the charging circuit. It follows that the lead/tissue resistance $R_L$ can be calculated using equation (1) below:

$$R_L = -\frac{Rx}{\frac{Rx}{R_r\left(\frac{V_i}{V_{RT}(0^+)}+1\right)+R_{SW}}+1} \quad (1)$$

When a constant voltage is applied to an RC circuit, the amount of current flowing through that circuit changes over time in a well-documented manner. Thus, as the charge contained in tank capacitor $C_T$ is released into the charging circuit from time t=0 to time t=$T_{PW}$, the charging current changes over time. The rate at which the current changes is determined by the resistances $R_T$, $R_{SW}$, and $R_L$ and capacitances $C_T$, $C_B$, and $C_L$.

Because the voltage drop across the shunt resistor at any point in time $V_{RT}(t)$ is directly proportional to the current through $R_T$ and because the resistances $R_T$, $R_{SW}$, and $R_L$ and capacitances $C_T$, $C_B$, and $C_L$ uniquely determine the charging current at time t=$T_{PW}$−, the Helmholtz capacitance $C_L$ may be calculated using equation (2) below. Because $R_X$ has a very high impedance compared with the remaining components in the circuit, little current flows through $R_X$. Thus, the presence of $R_X$ may be neglected for purposes of analyzing the Helmholtz capacitance $C_L$.

$$C_L = -\frac{C_T C_B}{C_T C_B \frac{R_T + R_{SW} + R_L}{T_{PW}} \ln\left(\frac{V_{RT}(T_{PW}-)[R_T + R_{SW} + R_L]}{V_i R_T}\right)+C_B + C_r} \quad (2)$$

where ln( ) is the natural logarithm function.

Following the charging pulse, sample-and-hold units U3 and U2 hold voltages $V_{RT}(0^+)$ and $V_{RT}(T_{PW}-)$, respectively. Using these measured values of $V_{RT}(0^+)$ and $V_{RT}(T_{PW}-)$ along with known values of $C_T$, $R_T$, and $R_{SW}$, the processor 470 calculates the lead/tissue resistance $R_L$ and the Helmholtz capacitance $C_L$ using equations (1) and (2), above. These calculations provide an accurate characterization of the lead/tissue impedance and assist physicians in monitoring lead integrity, device longevity, and current, charge, and energy delivered to the heart tissue.

The pulse generator 468 operates as described previously, and the processor 470 asserts sample3 at time t=0+ to measure the shunt resistor voltage $V_{RT}(0^+)$ at the beginning of the pulse period. Shortly after time t=$T_{PW}$, or at time t=$T_{PW}$−, the processor 470 asserts the sample1 control signal to cause and sample-and-hold unit U1 to record the voltage of tank capacitor $C_T$ via buffer U4 immediately following the pulse period. The time t=$T_{PW}$+ is preferably less than 10 μs after time t=$T_{PW}$. The tank capacitor voltage at time t=$T_{PW}$+, or $V_{CT}(T_{PW}+)$, represents the voltage across tank capacitor $C_T$ with respect to ground shortly after the pulse period. The measurement of $V_{RT}(0^+)$ allows the processor 470 to calculate the lead/tissue resistance $R_L$ as before, using equation (1). In the alternative embodiment, however, the processor 470 uses $V_{CT}(T_{PW}+)$ in equation (3), below, to estimate the Helmholtz capacitance $C_L$ either by generating a lookup table or by successive approximation, as will be explained below with respect to FIGS. 8A and 8B. Equation (3) governs the tank capacitor voltage at time t=$T_{PW}$+:

$$V_{Ct}(T_{PW}^+) = \frac{V_i(C_TC_B + C_TC_L)}{C_TC_B + C_TC_LC_BC_L} + \qquad (3)$$

$$V_i\left(1 - \frac{C_TC_B + C_TC_L}{C_TC_B + C_TC_L + C_BC_L}\right)e^{-\left(\frac{1}{C_T}+\frac{1}{C_B}+\frac{1}{C_L}\right)\frac{T_{PW}^+}{R_T+R_{PW}+R_L}}$$

where e is the base of the natural logarithm.

Figure 7:
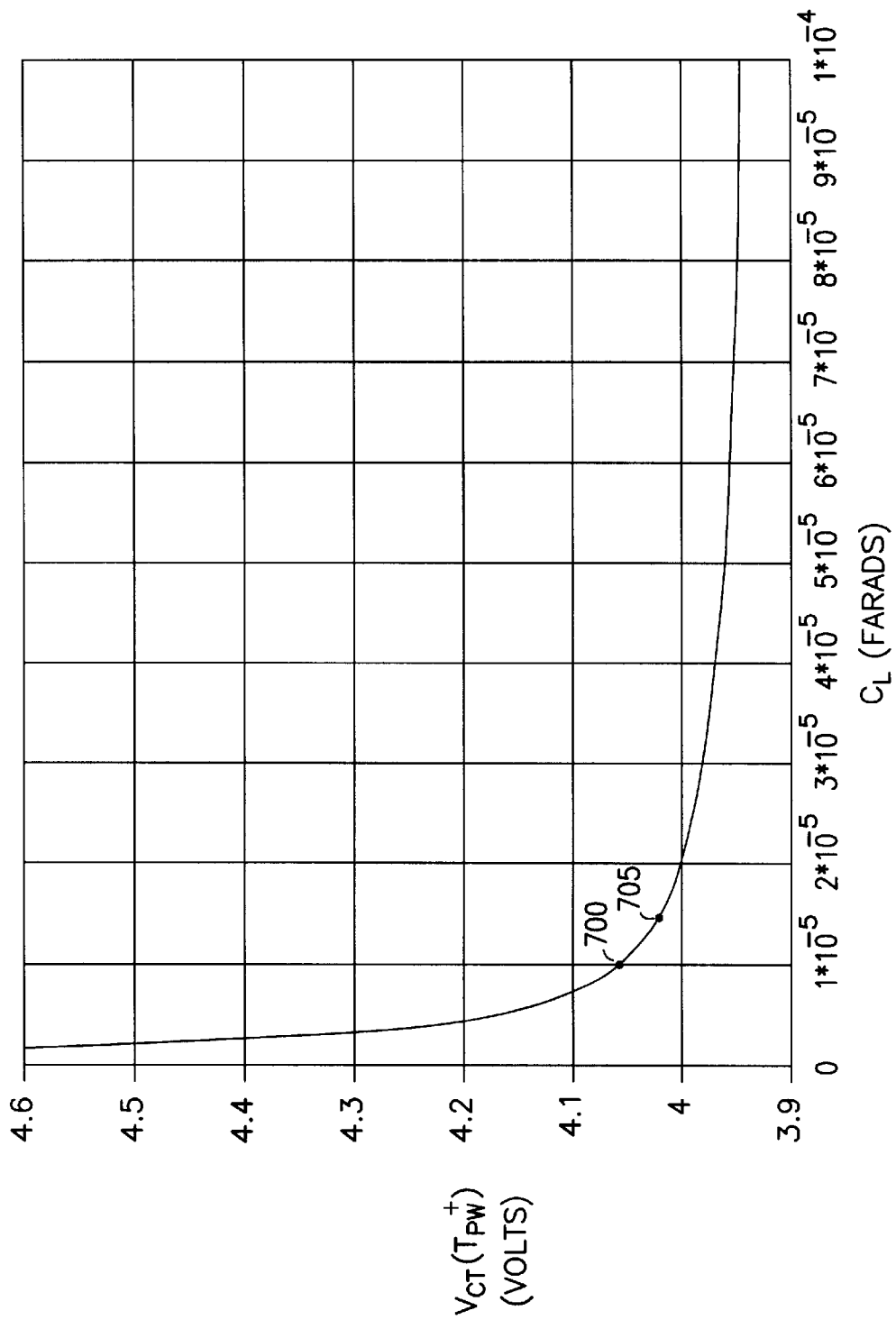
FIG. 7 is a graph of the voltage across the tank capacitor of FIG. 5 versus the Helmholtz voltage created in the heart tissue during cardiac stimulation.

FIG. 7 illustrates a graph of $V_{CT}(T_{PW}^+)$ versus $C_L$, according to equation (3). Note that for any point on the graph, an increase in Helmholtz capacitance $C_L$ results in an decrease in $V_{CT}(T_{PW}^+)$. For example, point 700 represents $C_L=10$ μF, $V_{CT}(T_{PW}^+)=4.06$. It can be seen that for any $C_L>10$ μF, $V_{CT}(T_{PW}^+)<4.06$. For instance, $C_L=15$ μF and $V_{CT}(T_{PW}^+)=4.02$ at point 705. Thus, $V_{CT}(T_{PW}^+)$ of equation (3) is said to monotonically decrease in Helmholtz capacitance $C_L$. It follows that any measured tank capacitor voltage $V_{CT}(T_{PW}^+)$ corresponds to a unique Helmholtz capacitance $C_L$ which may be calculated using the alternative embodiments presented herein.

After the processor 470 calculates the lead/tissue resistance $R_L$ using shunt resistor voltage measurement $V_{RT}(0^+)$ in equation (1), all the variables in equation (3) are known except for the Helmholtz capacitance $C_L$. To determine $C_L$, note that the right-hand side of equation (3) consists of an additive term $$A = \frac{V_i(C_TC_B + C_TC_L)}{C_TC_B + C_TC_L + C_BC_L},$$

a constant term $$K = V_i\left(1 - \frac{C_TC_B + C_TC_L}{C_TC_B + C_TC_L + C_BC_L}\right), \text{ and}$$

an exponential term $$E = e^{-\left(\frac{1}{C_T}+\frac{1}{C_B}+\frac{1}{C_L}\right)\frac{T_{PW}^+}{R_T+R_{SW}+R_L}}.$$

Because the Helmholtz capacitance $C_L$ is present in the additive, constant, and exponential terms in equation (3), there is no explicit algebraic solution for $C_L$. Hence, in one alternative embodiment, the processor 470 either generates or retrieves from memory a set of candidate estimates for Helmholtz capacitance $C_L$. The processor then evaluates the right-hand-side of equation (3) using each of the candidate estimates, recording the evaluation results into memory as a lookup table. The processor 470 estimates $C_L$ by determining which evaluation of equation (3) most closely matches the voltage $V_{CT}(T_{PW}^+)$ at the output of sample-and-hold unit U1. Because $V_{CT}(T_{PW}^+)$ in equation (3) decreases monotonically in $C_L$, the value of $C_L$ used in equation (3) to compute the $V_{CT}(T_{PW}^+)$ which most closely matches the $V_{CT}(T_{PW}^+)$ measured from U1 is a good estimate of the actual Helmholtz capacitance, $C_L$. Further, the processor 470 may be programmed to estimate the Helmholtz capacitance to any arbitrary degree of accuracy in this embodiment by evaluating equation (3) using numerous candidate values of $C_L$ which are sufficiently closely spaced.

Table I illustrates an exemplary lookup table using this alternative embodiment. To generate Table I, processor 470 uses known values of $V_i$, $C_T$, $C_B$, $R_T$, $R_{SW}$, and $T_{PW}$ which have been previously stored in processor memory. For purposes of this example, these values are $V_i=5$ V, $C_T=10$ F, $C_B=10$ μF, $R_T=22$ Ω, $R_{SW}=17$ Ω, and $T_{PW}+=1.5$ ms. Also, a set of candidate values for $C_L$ has been stored into the processor 470. For purposes of this example, these values are 1 μF, 2 μF, 3 μF, 4 μF, 5 μF, 6 μF, 7 μF, 8 μF, 9 μF, and 10 μF. Assuming also for this example that the processor uses the output of sample-and-hold unit U3 to calculate the lead/tissue resistance $R_L=500$ Ω, the processor evaluates equation (3) using each of the candidate values of $C_L$. Table I illustrates the resulting calculations of $V_{CT}(T_{PW}^+)$ as a function of the candidate $C_L$ values.

TABLE I

Example lookup table calculated from equation (3) and used to estimate $C_L$.

| $C_L$ (candidate) | $V_{CT}(T_{PW}^+)$ (calculated) |
|---|---|
| 1 μF | 4.5981 V |
| 2 μF | 4.3875 V |
| 3 μF | 4.2750 V |
| 4 μF | 4.2065 V |
| 5 μF | 4.1606 V |
| 6 μF | 4.1279 V |
| 7 μF | 4.1033 V |
| 8 μF | 4.0843 V |
| 9 μF | 4.0690 V |
| 10 μF | 4.0565 V |

In this example, the processor 470 measures from sample-and-hold unit U1 the actual tank capacitor voltage after the pulse, or $V_{CT}(T_{PW}^+)$, as 4.08 V. Scanning through the lookup table, the processor determines that the measured value of $V_{CT}(T_{PW}^+)$ most closely matches the lookup table value 4.0843 V. Because $C_L=8$ μF corresponds to $V_{CT}(T_{PW}^+)=4.0843$, the processor determines $C_L$ to be 8 μF in this example. Note that the impedance values, voltages, pulse width, and candidate $C_L$ values described herein are used only for this example and are not intended to limit the present invention. Furthermore, a lookup table of this embodiment may have any number and range of candidate $C_L$ values and should not be limited to the candidate $C_L$ values presented in the example.

In another alternative embodiment, the processor 470 calculates the lead/tissue resistance $R_L$ and measures the tank capacitor voltage following the pacing pulse $V_{CT}(T_{PW}^+)$ as before. In this embodiment, however, the processor uses equation (3) to iteratively estimate the Helmholtz capacitance $C_L$. First, the processor 470 substitutes an empirical estimate, preferably greater than the largest possible Helmholtz capacitance $C_L$, into the exponential term of equation (3). The processor then solves for an approximation of $C_L$ in the additive and constant terms. If the empirical estimate of $C_L$ agrees closely with the calculated approximation, then the processor uses the calculated approximation for the Helmholtz impedance.

Figure 8:
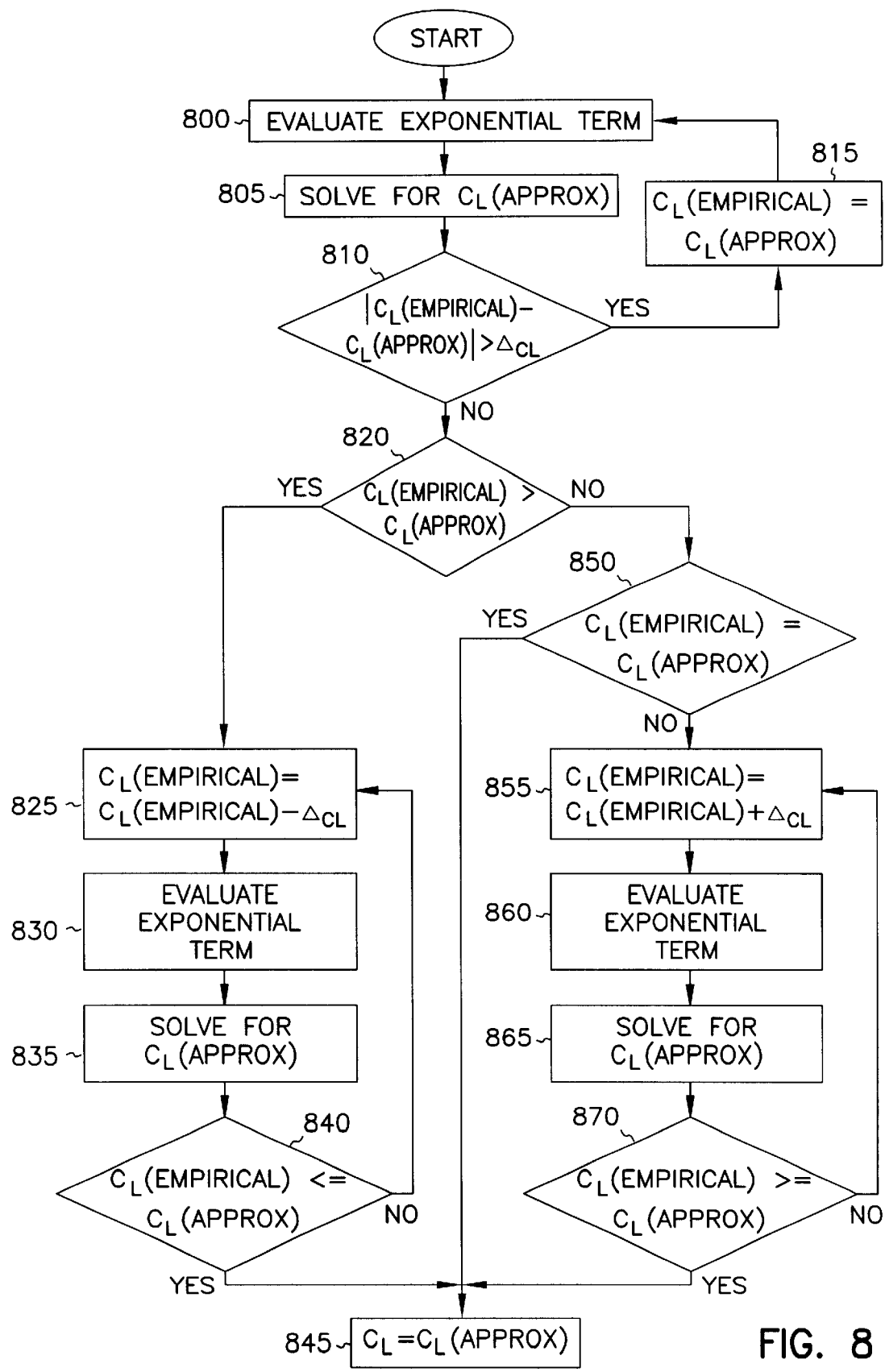
FIG. 8 is a flowchart describing an alternative embodiment for estimating the Helmholtz voltage using the apparatus of FIG. 5.

The flowchart of FIG. 8 illustrates the steps of successive approximation involved in this embodiment if the processor inserts the empirical estimate of $C_L$ into the exponential term of equation (3) and solves for an approximation of $C_L$ using the additive and constant terms. The flowchart begins at the "start" block. Moving to block 800, the processor 470 computes the value of the exponential term $$E = e^{-\left(\frac{1}{C_T}+\frac{1}{C_B}+\frac{1}{C_L(empirical)}\right)\frac{T_{PW}^+}{R_T+R_{SW}+R_L}}$$

using an initial empirical estimate of $C_L$, or $C_L$(empirical), that is preferably larger than the largest possible $C_L$ value. Using the calculated E, equation (3) may be expressed as in equation (4), below, which permits solving for $C_L$ algebraically.

$$V_{C_T}(T_{PW}^+) = \frac{V_i(C_T C_B + C_T C_L)}{C_T C_B + C_T C_L + C_B C_L} + V_i\left(1 - \frac{C_T C_B + C_T C_L}{C_T C_B + C_T C_L + C_B C_L}\right)E \quad (4)$$

In block 805, the processor 470 solves equation (4) algebraically for $C_L$, resulting in an approximation of the Helmholtz capacitance $C_L(\text{approx})$. The algebraic solution for $C_L$ in equation (4) is given by $C_L(\text{approx})$ in equation (5):

$$C_L(approx) = \frac{C_T C_B(V_i - V_{CT}(T_{PW}^+))}{(C_T + C_B)V_{CT}(T_{PW}^+) - V_i C_T - V_i E C_B} \quad (5)$$

In block 810, the processor computes the absolute difference between $C_L(\text{empirical})$ and $C_L(\text{approx})$, or $|C_L(\text{empirical})-C_L(\text{approx})|$. If the absolute difference between $C_L(\text{empirical})$ and $C_L(\text{approx})$ is greater than a predetermined limit $\Delta_{CL}$, which is preferably $\Delta_{CL}=1$ μF, then the processor 470 moves to block 815 and adjusts the empirical estimate $C_L(\text{empirical})$ so that the absolute difference between $C_L(\text{empirical})$ and $C_L(\text{approx})$ is smaller during a subsequent iteration. Because of the nature of this procedure, equation (5) always produces a value of $C_L(\text{approx})$ that is between $C_L(\text{empirical})$ and the true Helmholtz capacitance. Thus, $C_L(\text{empirical})$ is preferably adjusted by setting $C_L(\text{empirical})$ equal to $C_L(\text{approx})$, although other known methods of adjusting $C_L(\text{empirical})$ so that $C_L(\text{empirical})$ and $C_L(\text{approx})$ converge iteratively may be used as well. When $C_L(\text{empirical})$ is adjusted to produce a new $C_L(\text{empirical})$ in step 815, the processor 470 repeats steps 800, 805, 810, and 815 of the flowchart until $C_L(\text{approx})$ is within the predetermined limit $\Delta_{CL}$ of $C_L(\text{empirical})$.

Next moving to step 820, the processor 470 determines if $C_L(\text{empirical})$ is greater than $C_L(\text{approx})$. If $C_L(\text{empirical})$ is greater than $C_L(\text{approx})$ in step 820, then the current $C_L(\text{empirical})$ is larger than the true Helmholtz capacitance, and the processor moves to step 825. In step 825, $C_L(\text{empirical})$ is preferably adjusted by subtracting $\Delta_{CL}$ from $C_L(\text{empirical})$. Moving next to step 830, the processor 470 computes the value of the exponential term E as in step 800, using the updated $C_L(\text{empirical})$. From the calculated E, equation (3) may be expressed as in equation (4), which permits solving for $C_L$ algebraically. Hence, in block 835, the processor 470 solves equation (4) algebraically for $C_L$ to obtain an updated $C_L(\text{approx})$. As in step 805, the algebraic solution for $C_L$ in step 835 is given by $C_L(\text{approx})$ in equation (5).

Next moving to step 840, the processor 470 determines if $C_L(\text{empirical})$ is less than or equal to $C_L(\text{approx})$. Because step 835 always results in a $C_L(\text{approx})$ that is between $C_L(\text{empirical})$ and the true Helmholtz capacitance, the condition $C_L(\text{empirical})\leq C_L(\text{approx})$ indicates that the previous adjustment of $C_L(\text{empirical})$ in step 825 resulted in a $C_L(\text{empirical})$ which was less than or equal to the true Helmholtz capacitance. Accordingly, $C_L(\text{empirical})$ is guaranteed to be within $\Delta_{CL}$ below the true Helmholtz capacitance, and $C_L(\text{approx})$ is guaranteed to be between $C_L(\text{empirical})$ and the true Helmholtz capacitance. The processor thus moves to step 845, where the Helmholtz capacitance is estimated as $C_L=C_L(\text{approx})$. Alternatively, the Helmholtz capacitance may be estimated using the previous value of $C_L(\text{approx})$, which is guaranteed to be within $\Delta_{CL}$ above the true Helmholtz capacitance. If $C_L(\text{empirical})>C_L(\text{approx})$ in step 840, however, then the processor repeats back to step 825 to further adjust $C_L(\text{empirical})$.

Again examining step 820, if $C_L(\text{empirical})\leq C_L(\text{approx})$, then $C_L(\text{empirical})$ is less than or equal to the true Helmholtz capacitance, and the processor moves to step 850. From step 850, the processor 470 compares $C_L(\text{empirical})$ to $C_L(\text{approx})$. If $C_L(\text{empirical})=C_L(\text{approx})$, then both $C_L(\text{empirical})$ and $C_L(\text{approx})$ are equal to the true Helmholtz capacitance, and the processor 470 preferably estimates the Helmholtz capacitance as $C_L(\text{approx})$ in step 845. Alternatively, the processor 470 estimates the Helmholtz capacitance as $C_L(\text{empirical})$ in step 845. In addition, the Helmholtz capacitance may be estimated in step 845 as either the current or previous value of $C_L(\text{empirical})$, since these values are guaranteed to be within $\Delta_{CL}$ of the true Helmholtz capacitance. If $C_L(\text{empirical})$ is not equal to $C_L(\text{approx})$ in step 850, then the processor 470 moves to step 855. Steps 855 through 870 correspond approximately to steps 825 through 840, except that $C_L(\text{empirical})$ is assumed to be less than the true Helmholtz capacitance in steps 855 through 870 and is therefore adjusted in step 855 by adding $\Delta_{CL}$ to $C_L(\text{empirical})$.

Following step 855, the processor 470 moves to step 860 to compute the value of the exponential term E as in step 800, using the updated $C_L(\text{empirical})$. From the calculated E, equation (3) may be expressed as in equation (4), which permits solving for $C_L$ algebraically. Hence, in block 865, the processor 470 solves equation (4) algebraically for $C_L$ to obtain an updated $C_L(\text{approx})$. As in step 805, the algebraic solution for $C_L$ in step 865 is given by $C_L(\text{approx})$ in equation (5).

Next moving to step 870, the processor 470 determines if $C_L(\text{empirical})$ is greater than or equal to $C_L(\text{approx})$. Because step 865 always results in a $C_L(\text{approx})$ that is between $C_L(\text{empirical})$ and the true Helmholtz capacitance, the condition $C_L(\text{empirical})\geq C_L(\text{approx})$ indicates that the previous adjustment of $C_L(\text{empirical})$ in step 855 resulted in a $C_L(\text{empirical})$ which was greater than or equal to the true Helmholtz capacitance. Accordingly, $C_L(\text{empirical})$ is guaranteed to be within $\Delta_{CL}$ above the true Helmholtz capacitance, and $C_L(\text{approx})$ is guaranteed to be between $C_L(\text{empirical})$ and the true Helmholtz capacitance. The processor thus moves to step 845, where the Helmholtz capacitance is estimated as $C_L=C_L(\text{approx})$. Alternatively, the Helmholtz capacitance may be estimated using the previous value of $C_L(\text{approx})$, which is guaranteed to be within $\Delta_{CL}$ below the true Helmholtz capacitance. In addition, the Helmholtz capacitance may be estimated in step 845 as either the current or previous value of $C_L(\text{empirical})$, since these values are guaranteed to be within $\Delta_{CL}$ of the true Helmholtz capacitance. If $C_L(\text{empirical})<C_L(\text{approx})$ in step 870, however, then the processor repeats back to step 855 to further adjust $C_L$ empirical).

When the Helmholtz capacitance $C_L$ and load resistance $R_L$ have been determined, a plurality of parameters of importance for analyzing and optimizing a pacing system may be calculated, including the current delivered to the cardiac tissue at any instantaneous point in time, the average current delivered to the cardiac tissue over the duration of the pulse, the total charge and the total energy delivered to the cardiac tissue and to the leads, and the Helmholtz potential after pacing polarization. For instance, the current flowing through the heart tissue at time t, or $i_L(t)$, is given by equation (6), neglecting $R_X$:

$$i_L(t) \approx \frac{v_i}{R_T + R_{SW} + R_L} e^{-\frac{\left(\frac{1}{C_T} + \frac{1}{C_B} + \frac{1}{C_L}\right)}{R_T + R_{SW} + R_L} t} \quad (6)$$

where e is the base of the natural logarithm.

Neglecting $R_X$ as before, equation (7) represents the average current flowing through the heart tissue:

$$\bar{i}_L \approx \frac{v_i}{T_{PW}\left(\frac{1}{C_T} + \frac{1}{C_B} + \frac{1}{C_L}\right)} \left[1 - e^{-\frac{\left(\frac{1}{C_T} + \frac{1}{C_B} + \frac{1}{C_L}\right) T_{PW}}{R_T + R_{SW} + R_L}}\right] \quad (7)$$

where e is the base of the natural logarithm.

Again neglecting $R_X$, equation (8) represents the charge $Q_D$ delivered to the heart tissue from time $t=0$ to time $t=T_{PW}$.

$$Q_D \approx \frac{v_i}{\frac{1}{C_T} + \frac{1}{C_B} + \frac{1}{C_L}} \left[1 - e^{-\frac{\left(\frac{1}{C_T} + \frac{1}{C_B} + \frac{1}{C_L}\right) T_{PW}}{R_T + R_{SW} + R_L}}\right] \quad (8)$$

where e is the base of the natural logarithm.

Finally, the energy $J_D$ delivered to the heart tissue from time $t=0$ to time $t=T_{PW}$, neglecting $R_X$ as before, is given by equation (9):

$$J_D \approx \frac{v_i^2 R_L}{2(R_T + R_{SW} + R_L)\left[\frac{1}{C_T} + \frac{1}{C_B} + \frac{1}{C_L}\right]} \left[1 - e^{-\frac{2\left(\frac{1}{C_T} + \frac{1}{C_B} + \frac{1}{C_L}\right) T_{PW}}{R_T + R_{SW} + R_L}}\right] + \frac{Q_D^2}{2 C_L} \quad (9)$$

Thus, the present invention produces a very accurate impedance characterization of the lead/tissue interface, including both resistive and reactive impedance components. Further, since buffers U4 and U5 have high-impedance inputs coupled directly to the pulse generator 468, the present invention is adapted to perform impedance measurements during normal pacing and defibrillating operation and with minimal interference to the pulse generator 468. In addition, and importantly, because the impedance measurements occur during normal pacer operation, the pacer operation need not be suspended in order to collect impedance data.

Because the processor 470 controls the switches SW1, SW2, and SW3 and also the sample signals, the processor 470 may be easily programmed to calculate lead/tissue impedance whenever desired. For instance, the processor 470 may calculate the lead/tissue impedance during every $n^{th}$ pacing pulse, where n can be an arbitrary integer. The periodic impedance calculations can then be stored into main memory to be retrieved at a later date, perhaps by a physician who needs to verify or optimize the implantable device 400. Storing the calculations in memory also allows the processor 470 to perform statistical analyses which are useful for pacer maintenance, such as calculating minimum impedance measurements, maximum impedance measurements, and moving averages. In addition, if the implantable device 400 is capable of external control through telemetry with a device external to the body, the processor 470 can easily be programmed to calculate lead impedance during manually-induced test sequences. Hence, physicians have access to both long-term and immediate impedance data with which to optimize and maintain the implanted device.

The alternative embodiments described above allow the processor 470 to accurately calculate both the lead/tissue resistance $R_L$ as well as the Helmholtz capacitance $C_L$ to any arbitrary degree of accuracy. Further, the alternative embodiments do not require measurement of the shunt resistor voltage $V_{CT}(T_{PW}-)$ just prior to the end of the pulse at time $t=T_{PW}-$.

Numerous variations and modifications will become apparent to those skilled in the art once the above disclosure is fully appreciated. It is intended that the following claims be interpreted to embrace all such variations and modifications.

We claim:

1. An implantable apparatus for measuring a lead/tissue resistance, comprising:

a pulse generator including a shunt resistor, the pulse generator producing a voltage across the shunt resistor;

an impedance circuit including a high input impedance buffer circuit receiving the shunt resistor voltage and producing an output signal, the impedance circuit further including a sample-and-hold receiving the output signal from the buffer;

a memory for storing known values of impedance and voltage of circuit elements included in the pulse generator; and a processor to generate a sample-and-hold control signal for operating the sample-and-hold, the processor being coupled to the impedance circuit and memory, the processor to receive from the sample-and-hold at least one signal which the processor uses along with the known values to determine the lead/tissue resistance.

2. The apparatus of claim 1, wherein the high impedance buffer includes a voltage follower.

3. The apparatus of claim 2, wherein the voltage follower includes a unity-gain operational amplifier.

4. The apparatus of claim 1, wherein the processor generates the sample-and-hold control signal less than 10 μsec after the pulse generator begins a pulse.

5. The apparatus of claim 4, wherein the processor generates a further sample-and-hold control signal less than 10 μsec before the pulse generator ends the pulse.

6. The apparatus of claim 5, wherein the processor generates a still further control signal less than 10 μsec after the pulse generator ends the pulse.

7. The apparatus of claim 1, wherein the processor generates the sample-and-hold control signal less than 10 μsec before the pulse generator ends a pulse.

8. The apparatus of claim 7, wherein the processor generates a further sample-and-hold control signal less than 10 μsec after the pulse generator ends a pulse.

9. The apparatus of claim 1, wherein the processor generates the sample-and-hold control signal less than 10 μsec after the pulse generator ends a pulse.

10. The apparatus of claim 1, wherein the sample-and-hold operates to sample-and-hold the output signal from the buffer after the pulse generator begins a pulse, before the pulse generator ends the pulse and after the pulse generator ends the pulse.

11. The apparatus of claim 1, wherein the pulse generator includes a tank capacitor, an output switch having a resistance ($R_{SW}$), a discharge resistor ($R_X$), and a voltage source ($V_i$) for charging the tank capacitor, the output switch being connected between the tank capacitor and the discharge resistor, the lead/tissue resistance ($R_L$) being determined by the processor using the following equation:

$$R_L = -\frac{R_X}{\frac{R_X}{Rt\left(\frac{Vi}{V_{rt}}+1\right)+R_{SW}}+1}$$

wherein $R_t$ is the resistance of the shunt resistor and $V_{rt}$ is the voltage drop across the shunt resistor.

12. The apparatus of claim 11, wherein the voltage drop $V_{rt}$ is sampled by the sample-and-hold immediately after the pulse generator begins a pulse.

13. The apparatus of claim 11, wherein the voltage drop $V_{rt}$ is sampled by the sample-and-hold within 10 $\mu$sec after the pulse generator begins a pulse.

14. The apparatus of claim 1, wherein the lead/tissue resistance is determined by the processor using an equation which relates the lead/tissue resistance to a voltage provided by the sample-and-hold.

15. The apparatus of claim 1, wherein the shunt resistor is connected in parallel with the lead/tissue resistance.

* * * * *

UNITED STATES PATENT AND TRADEMARK OFFICE
CERTIFICATE OF CORRECTION

PATENT NO. : 6,788,972 B2
DATED : September 7, 2004
INVENTOR(S) : Prutchi et al.

It is certified that error appears in the above-identified patent and that said Letters Patent is hereby corrected as shown below:

Column 11,
Line 31, delete "CT" and insert -- $C_T$ --, therefor.
Line 32, delete "t=0" and insert -- $t=0^+$ --, therefor.
Line 36, delete "CT" and insert -- $C_T$ --, therefor.
Line 46, delete "$T_{PW}$" and insert -- $T_{PW}^+$, --, therefor.

Column 12,
Line 50, delete "t=0+" and insert -- $t=0^+$ --, therefor.
Line 53, delete "$T_{PW}^-$" and insert -- $T_{PW}^+$ --, therefor.

Signed and Sealed this

Fifteenth Day of February, 2005

JON W. DUDAS
*Director of the United States Patent and Trademark Office*